United States Patent
Misawa

(10) Patent No.: US 11,590,442 B2
(45) Date of Patent: Feb. 28, 2023

(54) SYSTEMS AND METHODS FOR PROVIDING FILTERED AIR TO AN ENCLOSURE FOR A PASSENGER OF A VEHICLE

(71) Applicant: The Boeing Company, Chicago, IL (US)

(72) Inventor: Culver T. Misawa, Everett, WA (US)

(73) Assignee: The Boeing Company, Chicago, IL (US)

( * ) Notice: Subject to any disclaimer, the term of this patent is extended or adjusted under 35 U.S.C. 154(b) by 350 days.

(21) Appl. No.: 16/886,120

(22) Filed: May 28, 2020

(65) Prior Publication Data

US 2021/0370212 A1 Dec. 2, 2021

(51) Int. Cl.
*B01D 46/00* (2022.01)
*B01D 46/12* (2022.01)
*B64D 11/06* (2006.01)
*B64D 13/06* (2006.01)
*B01D 39/12* (2006.01)
*A61L 9/20* (2006.01)

(52) U.S. Cl.
CPC ............ *B01D 46/0028* (2013.01); *A61L 9/20* (2013.01); *B01D 39/12* (2013.01); *B64D 11/0632* (2014.12); *B64D 13/06* (2013.01); *A61L 2209/12* (2013.01); *A61L 2209/14* (2013.01); *A61L 2209/16* (2013.01); *B01D 2279/65* (2013.01); *B64D 2013/0651* (2013.01)

(58) Field of Classification Search
CPC ............................ B01D 46/0028; B01D 46/12; B01D 2279/65; A61L 9/20; A61L 2209/14; B64D 11/0632; B64D 11/0626; B64D 2013/0625

USPC ................ 55/385.1, 385.2, DIG. 34; 96/224; 422/4; 15/313
See application file for complete search history.

(56) References Cited

U.S. PATENT DOCUMENTS

| | | | | |
|---|---|---|---|---|
| 3,462,920 A | * | 8/1969 | Douglas | F24F 3/163 55/467 |
| 3,724,172 A | * | 4/1973 | Wood | A61G 10/02 55/467 |
| 3,878,570 A | * | 4/1975 | Donnelly | A61G 11/00 219/217 |
| 3,893,457 A | * | 7/1975 | van der Waaij | A61G 13/108 55/416 |
| 5,005,470 A | * | 4/1991 | Denker | B08B 15/026 55/467 |
| 5,085,134 A | * | 2/1992 | Hofstra | F24F 7/06 454/67 |

(Continued)

OTHER PUBLICATIONS

Jen Murphy, "Hazmat Suits for Air Travel are Here", https://www.bloomberg.com/news/articles/2020-07-15/biovyzr-hazmat-suits-aim-to-make-flying-safer-during-coronavirus, retrieved from the Internet on Jul. 21, 2020.

(Continued)

*Primary Examiner* — Minh Chau T Pham
(74) *Attorney, Agent, or Firm* — McDonnell Boehnen Hulbert & Berghoff LLP

(57) ABSTRACT

Within examples, a system to provide filtered air to an enclosure for a passenger of a vehicle is described that includes a collapsible canopy hood attachable to a support structure of a vehicle, and a filter unit mounted to the support structure of the vehicle and having an output coupled to the collapsible canopy hood. The filter unit includes an air filtration component to filter air that is then output to the collapsible canopy hood.

20 Claims, 7 Drawing Sheets

(56) References Cited

U.S. PATENT DOCUMENTS

| | | | | |
|---|---|---|---|---|
| 5,160,517 | A | * | 11/1992 | Hicks .................. F24F 13/0604 5/423 |
| 6,039,776 | A | * | 3/2000 | Liue ........................ A24F 47/00 15/313 |
| 6,916,238 | B2 | * | 7/2005 | Korman .................. F24F 3/163 55/385.2 |
| 8,444,747 | B2 | * | 5/2013 | Kristensson ............. F24F 11/30 128/202.13 |
| 10,029,797 | B2 | | 7/2018 | Space et al. |
| 2010/0233019 | A1 | * | 9/2010 | Al-Thallab ........ B01D 46/0028 422/4 |
| 2011/0277634 | A1 | * | 11/2011 | Moyal .................... A45D 2/001 95/273 |
| 2012/0024154 | A1 | * | 2/2012 | Augustine ......... A61M 15/0083 95/273 |

OTHER PUBLICATIONS

BioVYZR 1.0, VYZR Technologies, https://www.vyzrtech.com/products/bio-vyzr, retrieved from the Internet on Jul. 21, 2020.

* cited by examiner

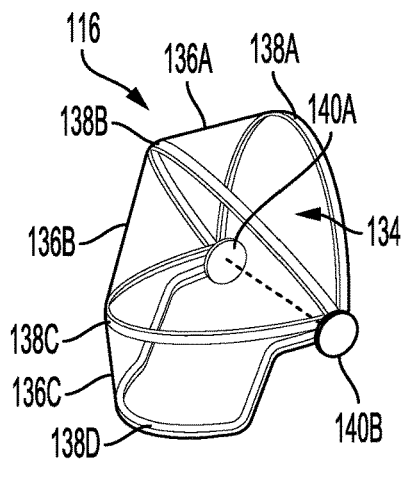
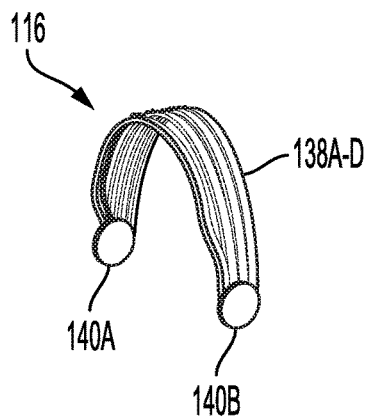
FIG. 5A
FIG. 5B
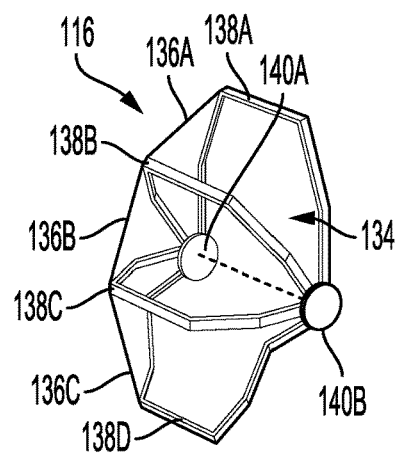
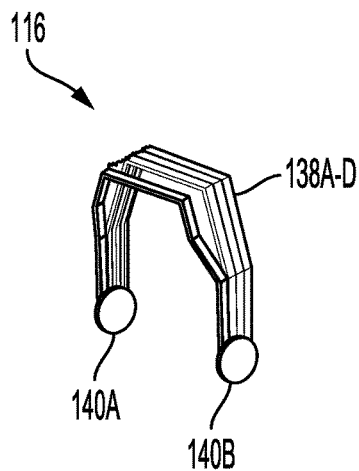
FIG. 6A
FIG. 6B
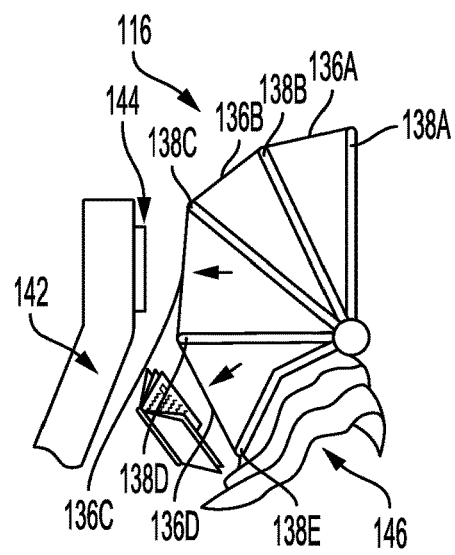
FIG. 7

SYSTEMS AND METHODS FOR PROVIDING FILTERED AIR TO AN ENCLOSURE FOR A PASSENGER OF A VEHICLE

FIELD

The present disclosure relates generally to vehicles (such as aircraft) that transport multiple passengers, and in particular, to methods and systems for managing air quality in the vehicles for each passenger.

BACKGROUND

Cabin air systems in example aircraft are designed to provide a comfortable cabin environment at cruising altitudes. In some examples, the cruising altitudes reach upwards of 40,000 feet. At these altitudes, the aircraft cabin is pressurized to enable passengers and crew to breathe normally. Air enters a passenger area from overhead distribution outlets that run a length of the aircraft cabin. The distribution outlets are designed to generate circular airflow patterns within the cabin. Air supplied to the cabin thus contains a mixture of re-circulated air from within the passenger cabin and air from outside the aircraft. Air is exhausted through air returns located in sidewalls near a floor of the cabin within some examples. The air returns can be located along the length of the aircraft cabin and on both sides of the aircraft cabin. In operation, air is supplied and exhausted from the passenger area on a continuous basis.

Other vehicles, such as trains and buses, have alternate air circulation systems that also tend to circulate air for purposes of passenger comfortability In many existing vehicles, there is only a centralized air filtration unit for the entire vehicle. The centralized air filtration unit is required to filter contaminants present in the air inside the vehicle including both external air introduced inside the vehicle as well as air re-circulated inside the vehicle.

SUMMARY

In an example, a system to provide filtered air to an enclosure for a passenger of a vehicle is described. The system includes a collapsible canopy hood attachable to a support structure of a vehicle, and a filter unit mounted to the support structure of the vehicle and having an output coupled to the collapsible canopy hood. The filter unit includes an air filtration component to filter air that is then output to the collapsible canopy hood.

In another example, a vehicle is described that includes an environmental control system (ECS), and a system to provide filtered air to an enclosure for a passenger. The system includes a collapsible canopy hood attachable to a support structure of the vehicle, and a filter unit mounted to the support structure of the vehicle and having an output coupled to the collapsible canopy hood. The filter unit includes an air filtration component to filter air received from the ECS that is then output to the collapsible canopy hood.

In another example, a method for providing filtered air to an enclosure for a passenger of a vehicle is described. The method includes enclosing, via a collapsible canopy hood, a head and at least a portion of a chest of a passenger, and the collapsible canopy hood is attachable to a support structure of a vehicle. The method also includes receiving, at a filter unit mounted to the support structure of the vehicle, air from an environmental control system (ECS) of the vehicle, and filtering, by an air filtration component of the filter unit, the air received from the ECS of the vehicle. The method also includes outputting filtered air from the filter unit into the collapsible canopy hood.

The features, functions, and advantages that have been discussed can be achieved independently in various examples or combined in various manners in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 5A illustrates a perspective view of the collapsible canopy hood in an unfolded configuration, according to an example implementation.

FIG. 5B illustrates a perspective view of the collapsible canopy hood of FIG. 5A in a folded configuration, according to an example implementation.

FIG. 6A illustrates a perspective view of another example of the collapsible canopy hood in an unfolded configuration, according to an example implementation.

FIG. 6B illustrates a perspective view of the collapsible canopy hood of FIG. 6A in a folded configuration, according to an example implementation.

FIG. 7 illustrates a side view of a portion the collapsible canopy hood installed in a vehicle, according to an example implementation.

DETAILED DESCRIPTION

Disclosed examples will now be described more fully hereinafter with reference to the accompanying drawings, in which some, but not all of the disclosed examples are shown. Indeed, several different examples are described and should not be construed as limited to the examples set forth herein. Rather, these examples are described so that this disclosure will be thorough and complete and will fully convey the scope of the disclosure to those skilled in the art.

Within examples, a self-contained system is described that provides individual air filtration for passengers of vehicles. The system includes a local filtering mechanism per passenger, in some examples, rather than using a common filtering system of the vehicle. The system includes a collapsible canopy hood attachable to a support structure of a vehicle, and a filter unit mounted to the support structure of the vehicle and having an output coupled to the collapsible canopy hood. The filter unit includes an air filtration component to filter air that is then output to the collapsible canopy hood.

Within examples, multiple systems are included on-board a multi-passenger vehicle, and each system provides a personalized ventilation environment for each passenger during travel on-board the multi-passenger vehicle. For example, the system creates a substantially sealed, filtered and pressurized environment or enclosure for each individual passenger.

Figure 1:
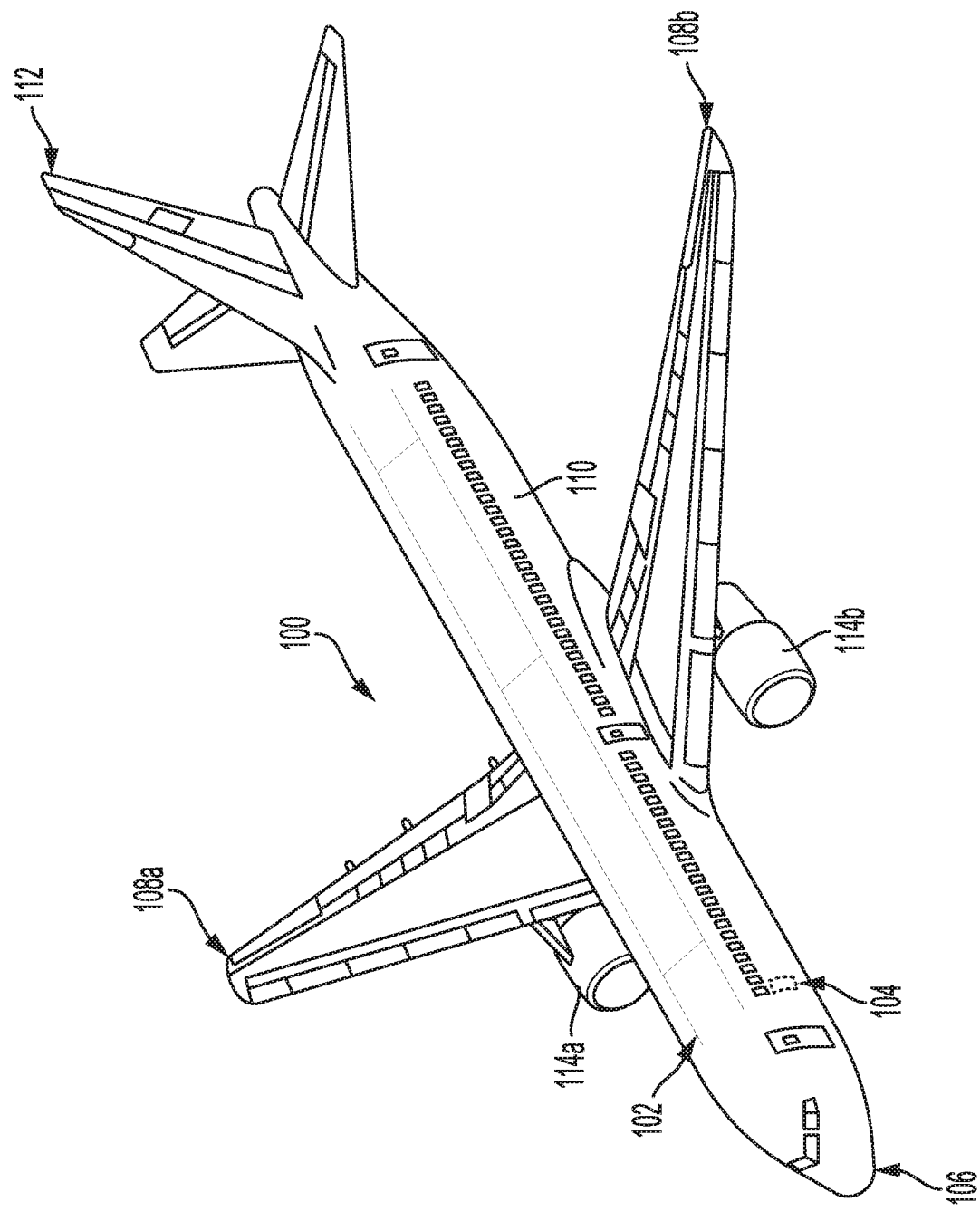
FIG. 1 illustrates an example of a vehicle, according to an example implementation.

Referring now to the figures, FIG. 1 illustrates an example of a vehicle 100, according to an example implementation. In the example shown in FIG. 1, the vehicle 100 is an aircraft. The vehicle 100 includes an environmental control system (ECS) 102 and a system 104 to provide filtered air to an enclosure for a passenger.

In the example in which the vehicle 100 is an aircraft, the aircraft includes a nose 106, wings 108a-b, a fuselage 110, a tail 112, and engines 114a-b, among other components. In examples, the ECS 102 runs a length of the aircraft, and has outlets at each individual seating areas of the aircraft or for each row of the aircraft. The system 104 is coupled or connected to the ECS 102 within examples described herein. The ECS 102 operates to provide clean or filtered air to the vehicle 100, and the system 104 is operable to receive the filtered air and provide further filtering of the air as well as an enclosure for respective passengers on-board the vehicle 100.

Although FIG. 1 illustrates an example of a commercial passenger aircraft, other types of aircraft are used with examples described herein. Moreover, although FIG. 1 illustrates the vehicle 100 as an aircraft, in other examples, the vehicle 100 is an automobile, a bus, a train, or a boat. The vehicle 100 may be any type of aircraft or ground vehicle transporting small (one, two or more people) or large groups of people.

Figure 2:
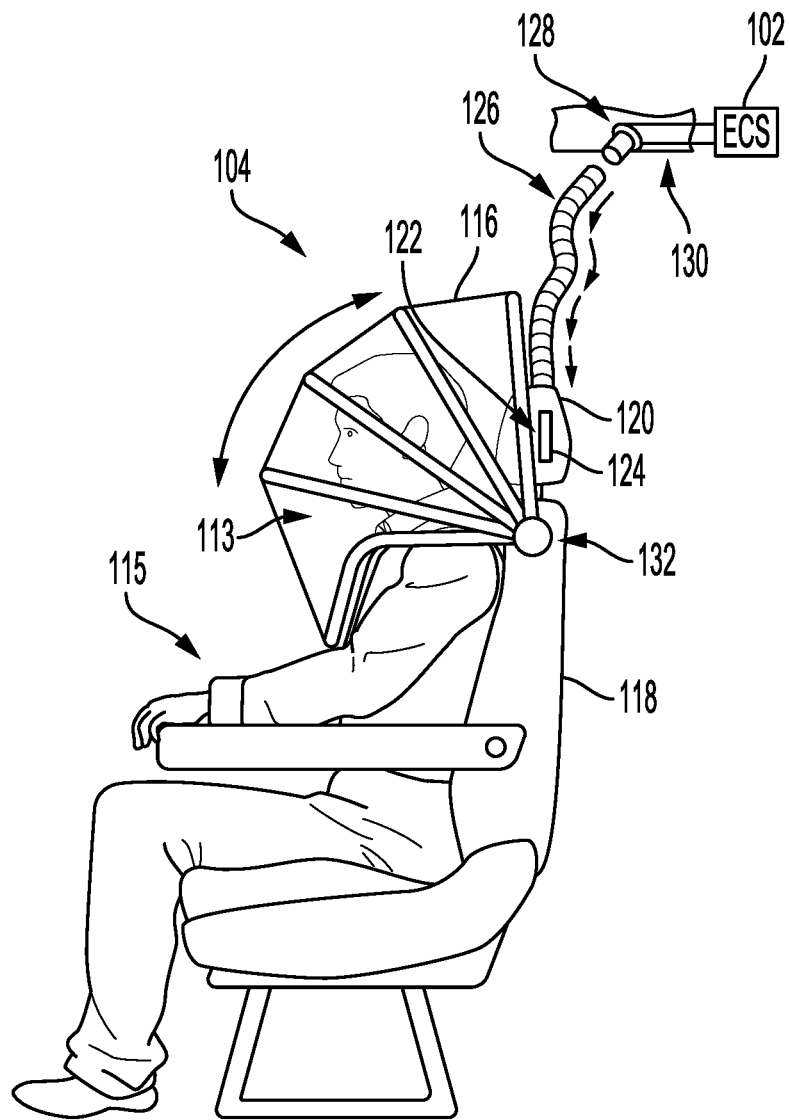
FIG. 2 illustrates a side view of an example of the system to provide filtered air to an enclosure for a passenger of the vehicle, according to an example implementation.
Figure 4:
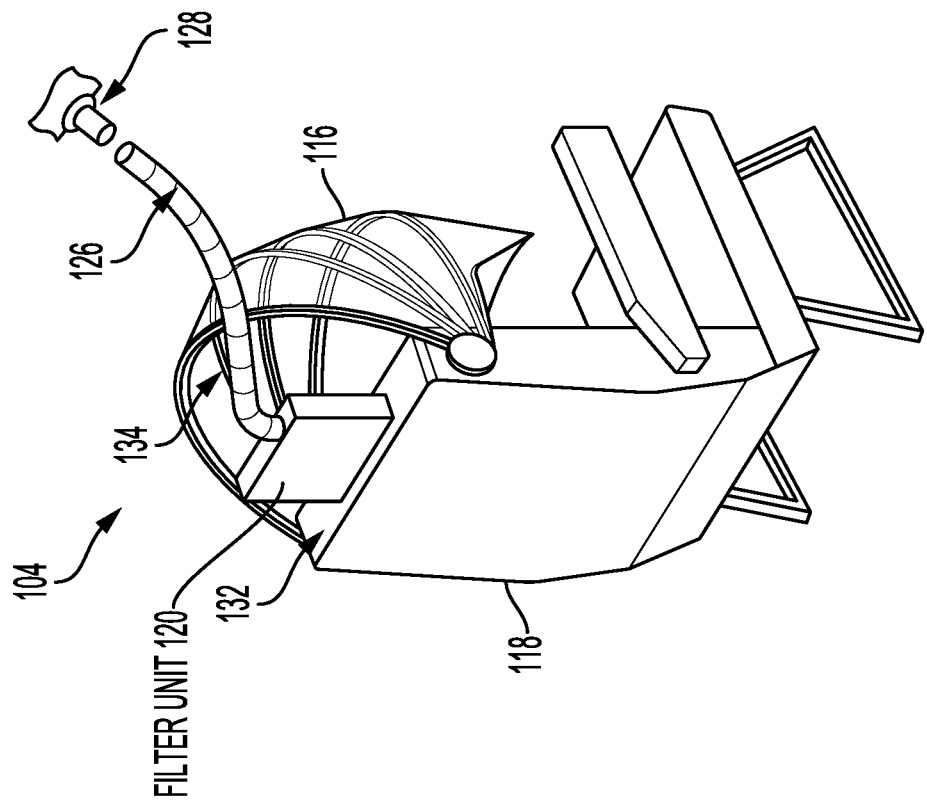
FIG. 4 illustrates a rear perspective view of the example of the system to provide filtered air to the enclosure for the passenger (not shown) of the vehicle, according to an example implementation.
Figure 3:
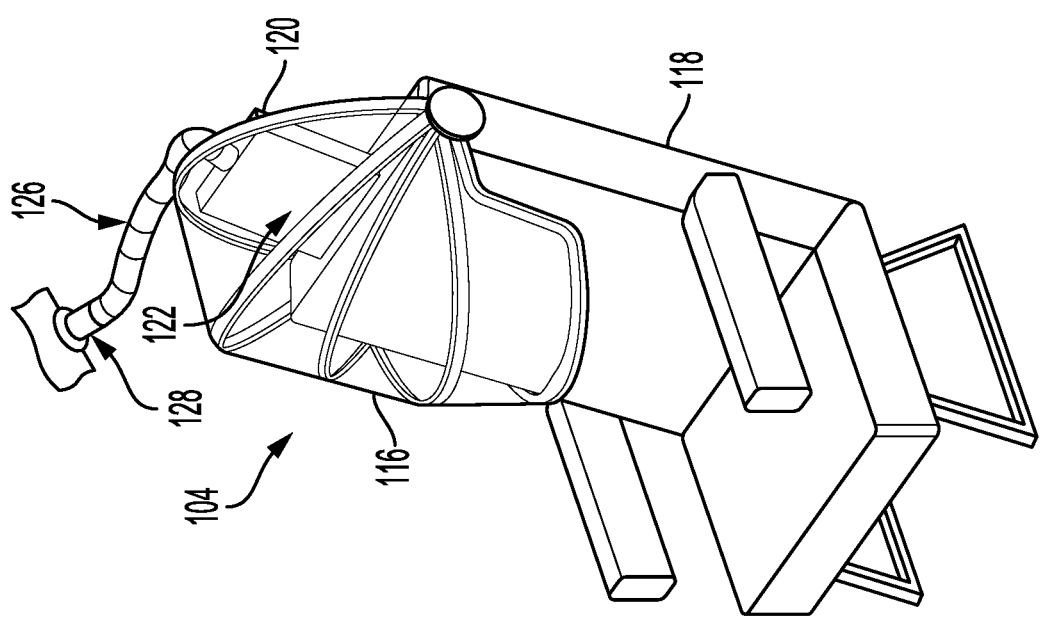
FIG. 3 illustrates a perspective view of the example of the system to provide filtered air to the enclosure for the passenger (not shown) of the vehicle, according to an example implementation.

FIG. 2 illustrates a side view of an example of the system 104 to provide filtered air to an enclosure 113 for a passenger 115 of the vehicle 100, according to an example implementation. FIG. 3 illustrates a perspective view of the example of the system 104 to provide filtered air to the enclosure 113 for the passenger 115 (not shown) of the vehicle 100, according to an example implementation. FIG. 4 illustrates a rear perspective view of the example of the system 104 to provide filtered air to the enclosure 113 for the passenger 115 (not shown) of the vehicle 100, according to an example implementation.

The system 104 includes a collapsible canopy hood 116 attachable to a support structure 118 of the vehicle 100, and a filter unit 120 mounted to the support structure 118 of the vehicle 100 and having an output 122 coupled to the collapsible canopy hood 116. In this manner, the filter unit 120 and the collapsible canopy hood 116 are supported by the support structure 118 and do not require complicated attachments enabling the system 104 to be installed on existing vehicle more easily. The filter unit 120 includes an air filtration component 124 to filter air that is then output to the collapsible canopy hood 116.

The collapsible canopy hood 116 can include a plastic material, a silicon material, a rubber material, an elastomeric material, or a combination of such materials, for example. These example materials enable the collapsible canopy hood 116 to be cleaned for subsequent uses.

In the example shown in FIG. 2, the support structure 118 of the vehicle 100 is a seatback of a seat of the vehicle 100. In this example, the filter unit 120 is mounted to a top portion 132 of the seatback of the seat of the vehicle 100. The filter unit 120 can be mounted or attached to the seatback of the seat of the vehicle 100 using an adhesive, mounting brackets with screws or snap-tight features, or other attachment mechanisms.

In alternate examples, the support structure 118 of the vehicle 100 includes a wall panel, a portion of a frame, or any structural component of the vehicle 100 where a passenger is present. Still further, in instances in which the vehicle 100 includes multiple installations of the system 104, the system 104 can be mounted to different types of support structures in the vehicle 100, such as to a seat, a wall panel, a portion of a frame, or any structural component of the vehicle 100.

In the example shown in FIG. 2, the filter unit 120 is mounted onto or integrated with the collapsible canopy hood 116. For example, the collapsible canopy hood 116 includes a panel 134 (illustrated in FIGS. 4, 5A and 6A) adjacent to the support structure 118 of the vehicle 100, and the panel 134 is coupled to the output 122 of the filter unit 120. The panel includes a vented opening to allow filtered air output of the filter unit 120 to be delivered into the collapsible canopy hood 116. In this example, the filter unit 120 is also connected or attached to the panel 134. The filter unit 120 can include a fabric or plastic covering that attaches to the panel 134, which also may be a plastic material as well. The collapsible canopy hood 116 and the filter unit 120 are then an integrated unit that can be installed and uninstalled jointly as one component.

As shown in the example illustrated in FIG. 2, the system 104 also includes a hose 126 connecting the filter unit 120 to the environmental control system (ECS) 102 of the vehicle 100 to receive the air. The hose 126 connects to the ECS 102 through a port 128 (e.g., an air vent) in a ceiling panel 130 of the vehicle 100. In some examples, the hose 126 also includes an electrical power cord to connect power to the filter unit 120. A power outlet can be included in the ceiling panel 130 as well.

The collapsible canopy hood 116 provides a substantially sealed environment for the passenger 115 to receive filtered air. In FIGS. 2-4, the collapsible canopy hood 116 is illustrated in an unfolded or extended configuration that is contoured to fit over at least a portion of shoulders and chest of the passenger 115.

In an example operation, the passenger 115 takes a seat and encloses a head and at least a portion of a chest of the passenger 115 with the collapsible canopy hood 116 by unfolding the collapsible canopy hood 116 to extend the collapsible canopy hood 116 over the head and chest of the passenger 115. Thus, when the collapsible canopy hood 116 is in the unfolded configuration, which is easily arranged by opening and unfolding the collapsible canopy hood 116, the collapsible canopy hood 116 provides the enclosure 113 for the passenger 115. The filter unit 120 then is operated to receive air from the ECS 102 of the vehicle 100, and to filter the air received from the ECS 102. Following, the filter unit 120 outputs filtered air from the filter unit 120 into the collapsible canopy hood 116, such as through the output 122, and then into the collapsible canopy hood 116 by passing through the panel 134. In operation, the system 104 is fluidly coupled to the ECS 102 of the vehicle to direct air from the ECS 102 to the filter unit 120 that cleans the air before delivering the air directly to the passenger 115 via the collapsible canopy hood 116. Note that air provided by the ECS 102 has already been filtered, and the system 104 beneficially further filters and isolates air being provided to the passenger 115 before such air mixes with air present in the cabin.

FIG. 5A illustrates a perspective view of the collapsible canopy hood 116 in an unfolded configuration, according to an example implementation. FIG. 5B illustrates a perspective view of the collapsible canopy hood 116 of FIG. 5A in a folded configuration, according to an example implementation.

In FIG. 5A, the collapsible canopy hood 116 includes segmented portions 136A, 136B, and 136C (136A-C) coupled to frame elements 138A, 138B, 138C, and 138D (138A-D) that enable the segmented portions 136A-C to fold together. For example, the segmented portion 136A extends between the frame element 138A and 138B, the segmented portion 136B extends between the frame element 138B and 138C, and the segmented portion 136C extends between the frame element 138C and 138D.

In one example, the segmented portions 136A-C include a foldable material, such as plastic, and the frame elements 138A-D include a solid material such as plastic, steel, aluminum, etc. In this example, the frame elements couple to a hinge, such as the frame elements 138A-D coupling to hinges 140A-B, and are rotatable about the hinge 140A-B to fold the segmented portions 136A-C together. In one example, the hinge 140A-B connects to the support structure 118 of the vehicle 100.

The frame elements 138A-D include a first frame element 138D that is contoured to fit over at least a portion of shoulders and chest of the passenger 115. Other frame elements (e.g., the frame elements 138A-C) include arcuate, rounded, or curved configurations to bow outward such that when the collapsible canopy hood 116 is in the unfolded configuration, an internal volume of the collapsible canopy hood 116 is comfortable for the passenger 115.

The collapsible canopy hood 116 further includes the panel enclosed within one of the frame elements (e.g., the frame element 138A) adjacent to the support structure 118 of the vehicle 100.

In the folded configuration, as shown in FIG. 5B, the collapsible canopy hood 116 sits upright, for example. Within examples, in the folded configuration, the collapsible canopy hood 116 is upright and enables the passenger 115 to stand up or leave the seating area easily.

FIG. 6A illustrates a perspective view of another example of the collapsible canopy hood 116 in an unfolded configuration, according to an example implementation. FIG. 6B illustrates a perspective view of the collapsible canopy hood 116 of FIG. 6A in a folded configuration, according to an example implementation.

The frame elements 138A-D in the example shown in FIGS. 6A-6B include straight portions coupled by curved corners to provided angled frame elements. Using the configuration of the frame elements 138A-D as shown in FIG. 6A-6B will provide less viewing distortion through the segmented portions 136A-C, in some examples.

As mentioned, the collapsible canopy hood 116 encloses a head and at least a portion of a chest of the passenger 115 when in the unfolded configuration. In other examples, the collapsible canopy hood 116 is larger and includes more segmented portions 136A-C so that the collapsible canopy hood 116 encloses a larger portion of the passenger 115, such as also enclosing arms, hands, and torso of the passenger 115.

FIG. 7 illustrates a side view of a portion the collapsible canopy hood 116 installed in a vehicle 100, according to an example implementation. In the example shown in FIG. 7, the collapsible canopy hood 116 includes one more frame element and one more segmented portion as compared to prior illustrations. Thus, the collapsible canopy hood 116 includes the frame elements 138A-E and the segmented portions 136A-D.

In FIG. 7, the collapsible canopy hood 116 is installed and connected to the support structure 118 (not shown) of the vehicle 100. In this example, the support structure 118 is a seat and the vehicle 100 is the aircraft. Another seat 142 is in front of the passenger 115 (not shown). The seat 142 includes an information screen 144 on a back of the seat 142. With the collapsible canopy hood 116 in the unfolded configuration, as shown in FIG. 7, and enclosing the head of the passenger 115, the passenger 115 views the information screen 144 by looking through the segmented portions 136A-D of the collapsible canopy hood 116. Thus, the segmented portions 136A-D are a clear or see-through material.

As mentioned, the collapsible canopy hood 116 provides a substantially sealed environment for the passenger 115 to receive filtered air. However, air can leak out at areas where the collapsible canopy hood 116 contacts the passenger 115 so that no physical air exhaust mechanism is needed.

In one example, the frame element 138E (lowest frame element) is contoured over shoulders of the passenger 115, and is used as a clip onto which a blanket 146 is attached. For example, and aircraft blanket (provided to passengers) can be clipped to the frame element 138E to create a further barrier between the collapsible canopy hood 116 and the passenger 115.

Figure 8:
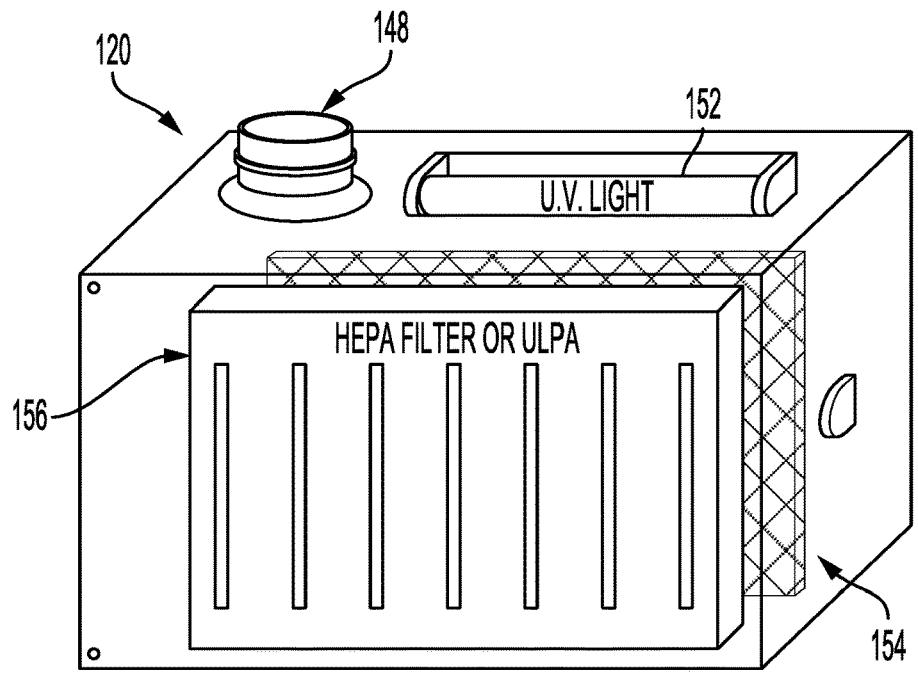
FIG. 8 illustrates a perspective view of the filter unit, according to an example implementation.
Figure 9:
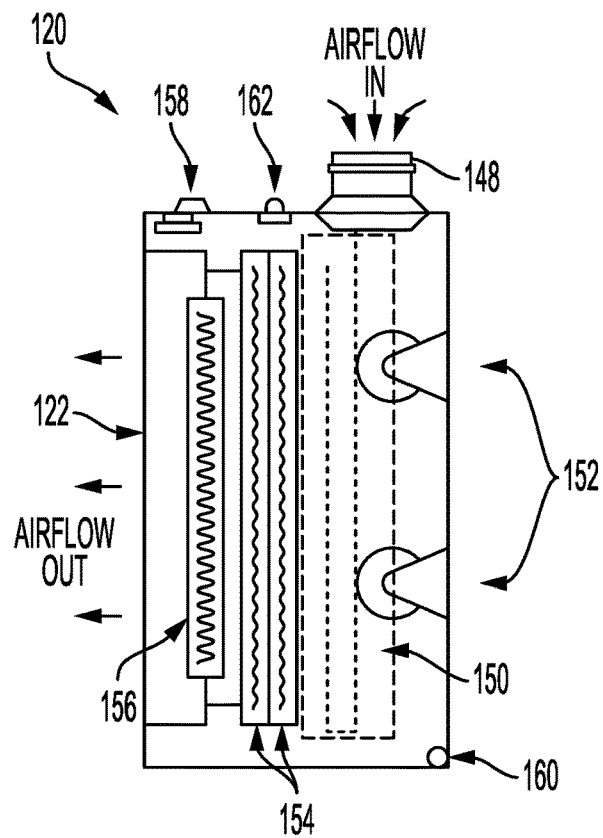
FIG. 9 illustrates a side of the filter unit, according to an example implementation.

FIG. 8 illustrates a perspective view of the filter unit 120, according to an example implementation. FIG. 9 illustrates a side of the filter unit 120, according to an example implementation.

The filter unit 120 includes an inlet 148 that connects or couples to the hose 126 to receive air from the ECS 102. The filter unit 120 includes a serpentine airflow pathway 150 internal to the filter unit 120, and once air enters the filter unit 120, the air travels through the serpentine airflow pathway 150.

The air filtration component 124 can take many forms. In one example, the air filtration component 124 of the filter unit 120 includes an ultraviolet light source 152. In FIG. 9, two ultraviolet light bulbs or tubes are shown. As the air travels through the serpentine airflow pathway 150, the air within the serpentine airflow pathway 150 is exposed to ultraviolet light from the ultraviolet light source 152. With ultraviolet light having a wavelength in a range of 200-400 nanometers (nm), the ultraviolet light from the ultraviolet light source 152 can filter the air by disinfecting the air through inactivation of microorganisms present in the air. The serpentine airflow pathway 150 provides a longer path for air to travel so that the air is exposed to ultraviolet light for a longer time period.

In another example, the air filtration component 124 of the filter unit 120 includes a mesh filter 154. The mesh filter 154 can include a copper mesh traps or micromesh filter that captures and filters micro-particles present in the air.

In another example, the air filtration component 124 of the filter unit 120 includes a high-efficiency particulate air (HEPA) filter 156 or an ultra-low particulate air (ULPA) filter. The filter unit 120 can include labeling with service dates, if necessary, indicating when the HEPA filter 156 should be changed.

Still further, the air filtration component 124 of the filter unit 120 can include a combination of any of the ultraviolet light source 152, the mesh filter 154, and the HEPA (or ULPA) filter 156. FIGS. 8-9 illustrate all of the ultraviolet light source 152, the mesh filter 154, and the HEPA (or ULPA) filter 156 being used, but fewer than all of these forms of air filtration components 124 can be used as well. Air travels in through the inlet 148 and is cleaned by the ultraviolet light source 152, the mesh filter 154, and the HEPA (or ULPA) filter 156, and then output through the output 122. Thus, air received into the filter unit 120 is filtered so that air output to the passenger 115 is clean air to reduce spread of any infection.

The filter unit 120 includes an access panel lock 158 and a panel hinge 160 to enable access to internal components of the filter unit 120, such as to change a filter, for example.

The filter unit 120 can be triggered to operate (e.g., turn on the ultraviolet light source 152 via power received from the electrical power cord of the hose 126) once the collapsible canopy hood 116 is extended and arranged in the unfolded configuration, as shown in FIGS. 2-4. As an example, the hinge 140A-B includes an internal switch that is turned on by extending the frame elements 138A-E causing the collapsible canopy hood 116 to be in the unfolded configuration, and is turned off by folding the frame elements 138A-E causing the collapsible canopy hood 116 to be in the folded configuration. In some examples, the hinge 140A-B is in electrical communication with the filter unit 120 or the ultraviolet light source 152 to trigger operation of the ultraviolet light source 152.

The filter unit 120 can also include a light indicator 162 that shows when the ultraviolet light source 152 is in operation. For instance, the light indicator 162 includes a plastic lens in port of window of a housing of the filter unit 120 so that when the ultraviolet light is on, light will shine through the lens so a passenger can see that the ultraviolet light source 152 is operating.

In examples where the filter unit 120 does not include the ultraviolet light source 152 and does not require power to operate, the filter unit 120 can be a passive filter unit utilizing one or more of the mesh filter 154 and the HEPA (or ULPA) filter 156 to clean the air, for example.

Figure 10:
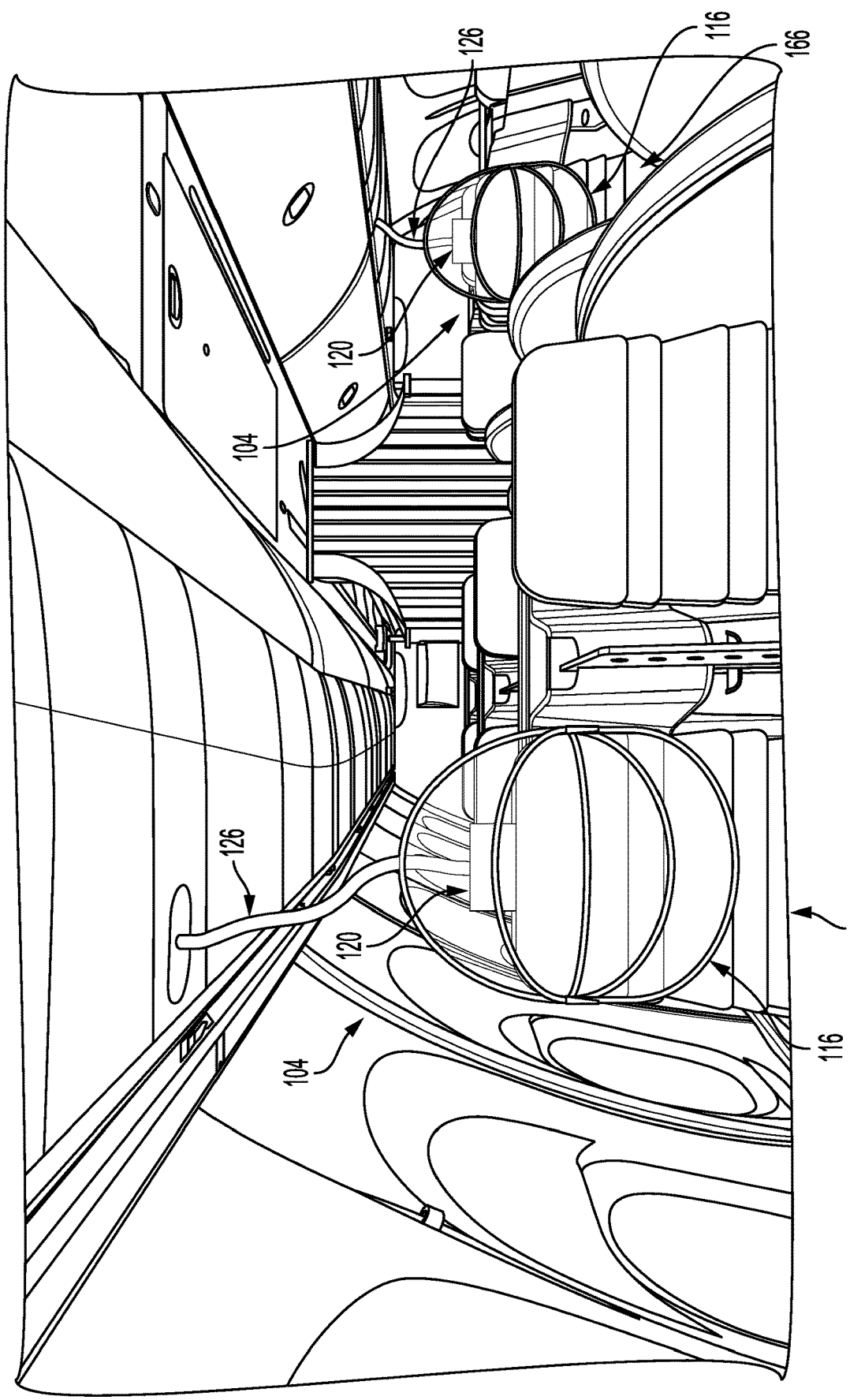
FIG. 10 illustrates an internal view of the vehicle, according to an example implementation.

FIG. 10 illustrates an internal view of the vehicle 100, according to an example implementation. In this example, the vehicle 100 is an aircraft, and the illustration in FIG. 10 shows an internal view of the fuselage 110 and seating area for passengers. As shown, a seat 164 includes the system 104 and another seat 166 includes the system 104. The system 104 enables passengers seated at the seat 164 or the seat 166 to be isolated from other passengers. Thus, in some examples, the system 104 is included in the vehicle 100 at selected seats.

Every seat in the vehicle 100 can include the system 104. In an example where the vehicle 100 has a plurality of seats, and the seat 164 is one of the plurality of seats, the vehicle 100 also includes a plurality of systems to provide filtered air to respective enclosures for respective passengers, where the system 104 is one of the plurality of systems. A respective system is coupled to a respective seat of the plurality of seats, and each system provides a substantially sealed enclosure for the respective passenger to substantially isolate airflow of passengers from each other.

Figure 11:
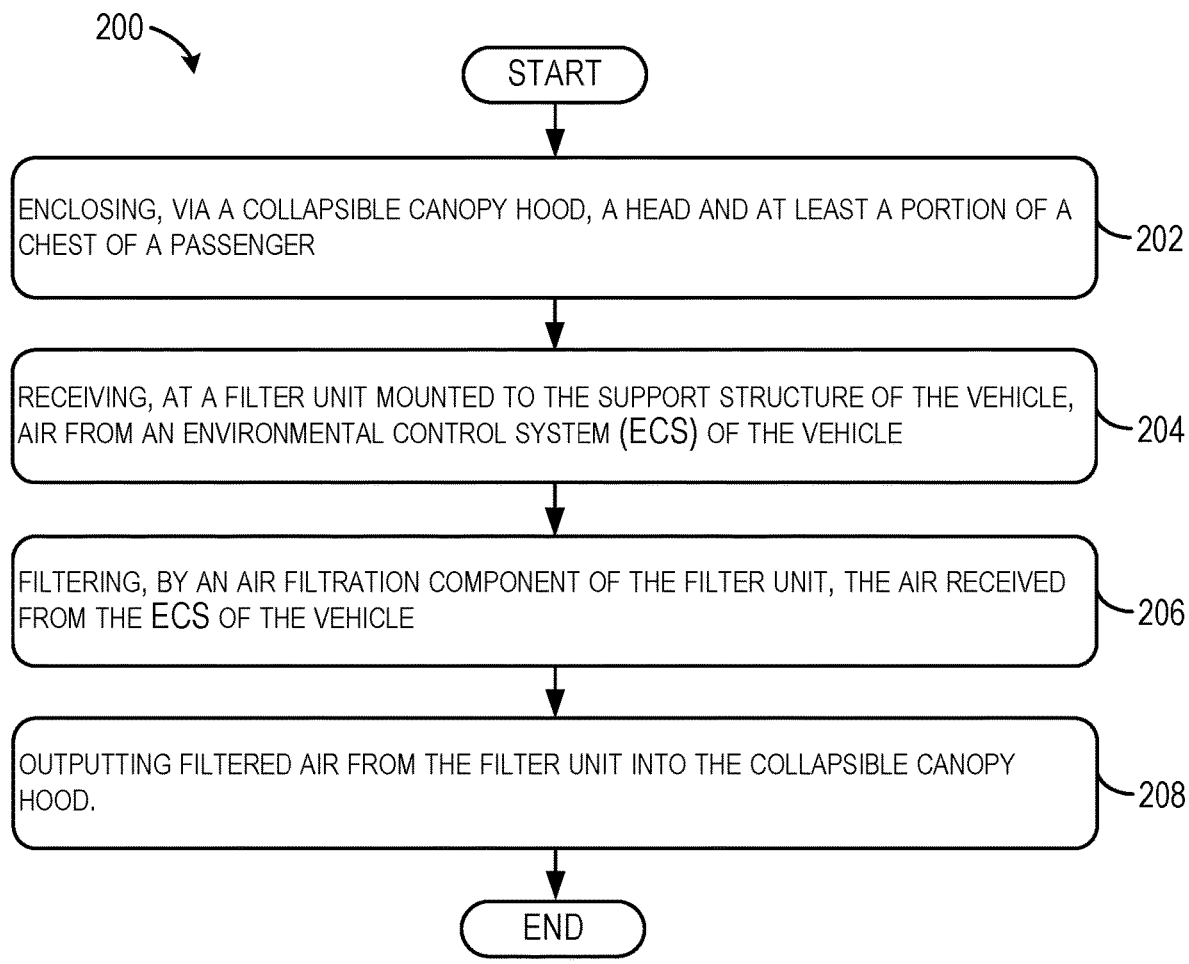
FIG. 11 shows a flowchart of an example of a method for providing filtered air to the enclosure for the passenger of the vehicle, according to an example implementation.

FIG. 11 shows a flowchart of an example of a method 200 for providing filtered air to the enclosure 113 for the passenger 115 of the vehicle 100, according to an example implementation. Method 200 shown in FIG. 11 presents an example of a method that could be used with the vehicle 100 shown in FIG. 1 and with the system 104 shown in FIGS. 2-5, for example. Further, devices or systems are used or configured to perform logical functions presented in FIG. 11. In some instances, components of the devices and/or systems are configured to perform the functions such that the components are actually configured and structured (with hardware and/or software) to enable such performance. In other examples, components of the devices and/or systems are arranged to be adapted to, capable of, or suited for performing the functions, such as when operated in a specific manner. Method 200 includes one or more operations, functions, or actions as illustrated by one or more of blocks 202-208. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 202, the method 200 includes enclosing, via the collapsible canopy hood 116, a head and at least a portion of a chest of the passenger 115. The collapsible canopy hood 116 is attachable to the support structure 118 of the vehicle 100 so as to be positioned proximate a seating area of the passenger 115.

As described above, the collapsible canopy hood 116 includes the segmented portions 136A-C coupled to the frame elements 138A-D that enable the segmented portions 136A-C to fold together. In some examples, enclosing, via the collapsible canopy hood 116, the head and at least the portion of the chest of the passenger 115 includes rotating the frame elements 138A-D about the hinge 140A-B to unfold the segmented portions 136A-C.

At block 204, the method 200 includes receiving, at the filter unit 120 mounted to the support structure 118 of the vehicle 100, air from the environmental control system (ECS) 102 of the vehicle 100.

At block 206, the method 200 includes filtering, by the air filtration component 124 of the filter unit 120, the air received from the ECS 102 of the vehicle 100

At block 208, the method 200 includes outputting filtered air from the filter unit 120 into the collapsible canopy hood 116.

Within examples, the system 104 is also easily installed or removed, and can be retrofitted to existing vehicles. In addition, using materials such as plastic and rubber, the system 104 is low cost to fabricate and adapt to any specific seating configuration. Moreover, beneficially, use of the system 104 does not require any modification to an air or environmental control system of the vehicle.

Note that although this disclosure has described use of the methods and systems for use on aircraft, the same methods and systems functions apply equally on board any type of vehicle in order to provide filtered air to an enclosure for a passenger. Within other examples, the methods and systems described herein find use within non-vehicles or stationary areas to provide filtered air to an enclosure for a passenger, such as for a stretcher or bed for medical purposes.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A system to provide filtered air to an enclosure for a passenger of a vehicle, the system comprising:
   a collapsible canopy hood attachable to a support structure of a vehicle, wherein the collapsible canopy hood is configurable into a folded configuration to sit upright and into an unfolded configuration to enclose a head and at least a portion of a chest of a passenger;
   a filter unit mounted to the support structure of the vehicle and having an output coupled to the collapsible canopy hood, the filter unit including an air filtration component to filter air that is then output to the collapsible canopy hood;
   a hose connecting the filter unit to an environmental control system (ECS) of the vehicle to receive the air, wherein the hose includes an electrical power cord to further provide power to the filter unit, and
   wherein the filter unit is triggered to operate via the power received from the electrical power cord of the hose once the collapsible canopy hood is arranged in the unfolded configuration.

2. The system of claim 1, wherein the support structure of the vehicle is a seatback of a seat of the vehicle.

3. The system of claim 1, wherein the collapsible canopy hood provides a substantially sealed environment for the passenger to receive filtered air.

4. The system of claim 1, wherein the collapsible canopy hood includes segmented portions coupled to frame elements that enable the segmented portions to fold together.

5. The system of claim 4, wherein the frame elements couple to a hinge and are rotatable about the hinge to fold the segmented portions together.

6. The system of claim 5, wherein the hinge connects to the support structure of the vehicle.

7. The system of claim 4, wherein the frame elements include a first frame element that is contoured to fit over at least a portion of shoulders and chest of a passenger.

8. The system of claim 4, wherein the collapsible canopy hood includes a panel enclosed within one of the frame elements adjacent to the support structure of the vehicle, wherein the panel is coupled to the output of the filter unit.

9. The system of claim 8, wherein the panel includes a vented opening to allow filtered air output of the filter unit to be delivered into the collapsible canopy hood.

10. The system of claim 1, wherein the support structure of the vehicle is a seatback of a seat of the vehicle, and wherein the filter unit is mounted to a top portion of the seatback of the seat of the vehicle.

11. The system of claim 1, wherein the air filtration component includes a high-efficiency particulate air (HEPA) filter.

12. The system of claim 1, wherein the air filtration component includes an ultra-low particulate air (ULPA) filter.

13. The system of claim 1, wherein the air filtration component includes an ultraviolet light source.

14. The system of claim 13, wherein the filter unit includes a serpentine airflow pathway internal to the filter unit, and air within the serpentine airflow pathway is exposed to ultraviolet light from the ultraviolet light source.

15. A vehicle comprising:
    an environmental control system (ECS); and
    a system to provide filtered air to an enclosure for a passenger, the system including:
        a collapsible canopy hood attachable to a support structure of a vehicle, wherein the collapsible canopy hood is configurable into a folded configuration to sit upright and into an unfolded configuration to enclose a head and at least a portion of a chest of a passenger;
        a filter unit mounted to the support structure of the vehicle and having an output coupled to the collapsible canopy hood, the filter unit including an air filtration component to filter air received from the ECS that is then output to the collapsible canopy hood;
        a hose connecting the filter unit to the ECS of the vehicle to receive the air, wherein the hose includes an electrical power cord to further provide power to the filter unit, and
        wherein the filter unit is triggered to operate via the power received from the electrical power cord of the hose once the collapsible canopy hood is arranged in the unfolded configuration.

16. The vehicle of claim 15, wherein the support structure of the vehicle is a seatback of a seat of the vehicle, and the vehicle further comprises:
    a plurality of seats, wherein the seat is one of the plurality of seats; and
    a plurality of systems to provide filtered air to respective enclosures for respective passengers, wherein the system is one of the plurality of systems, and wherein a respective system is coupled to a respective seat of the plurality of seats, and
    wherein each system provides a substantially sealed enclosure for the respective passenger to substantially isolate airflow of passengers from each other.

17. The vehicle of claim 15, wherein the hose connects to the ECS through a port in a ceiling panel of the vehicle.

18. A method for providing filtered air to an enclosure for a passenger of a vehicle, the method comprising:
    enclosing, via a collapsible canopy hood, a head and at least a portion of a chest of a passenger, wherein the collapsible canopy hood is attachable to a support structure of a vehicle, wherein the collapsible canopy hood is configurable into a folded configuration to sit upright and into an unfolded configuration to enclose the head and at least the portion of the chest of the passenger;

receiving, at a filter unit mounted to the support structure of the vehicle, air from an environmental control system (ECS) of the vehicle via a hose connecting the filter unit to the ECS of the vehicle to receive the air, wherein the hose includes an electrical power cord to further provide power to the filter unit;

based on the collapsible canopy hood being arranged in the unfolded configuration, the filter unit being triggered to operate via the power received from the electrical power cord of the hose and filtering, by an air filtration component of the filter unit, the air received from the ECS of the vehicle; and outputting filtered air from the filter unit into the collapsible canopy hood.

19. The method of claim 18, wherein the collapsible canopy hood includes segmented portions coupled to frame elements that enable the segmented portions to fold together, and wherein enclosing, via the collapsible canopy hood, the head and at least the portion of the chest of the passenger comprises:

rotating the frame elements about a hinge to unfold the segmented portions.

20. The system of claim 5, wherein the hinge includes an internal switch that is turned on by extending the frame elements causing the collapsible canopy hood to be in the unfolded configuration, and is turned off by folding the frame elements causing the collapsible canopy hood to be in the folded configuration.

* * * * *